United States Patent [19]

Sluka et al.

[11] Patent Number: 5,321,129
[45] Date of Patent: Jun. 14, 1994

[54] ALKYL-SUBSTITUTED ARYL-SACCHARIDES, SURFACE-ACTIVE AGENTS WHICH CONTAIN SUCH SACCHARIDES AND THEIR USE IN DIAGNOSTIC TESTS

[75] Inventors: Peter Sluka, Weilheim; Hans-Georg Batz; Bernd Vogt, both of Tutzing, all of Fed. Rep. of Germany

[73] Assignee: Boehringer Mannheim GmbH, Mannheim-Waldhof, Fed. Rep. of Germany

[21] Appl. No.: 882,874

[22] Filed: May 14, 1992

[30] Foreign Application Priority Data

May 17, 1991 [DE] Fed. Rep. of Germany ....... 4116257

[51] Int. Cl.$^5$ .................. C07H 15/18; C11D 3/22; A61K 49/00
[52] U.S. Cl. ..................... 536/41; 424/531; 435/2; 252/174.17
[58] Field of Search ............ 536/4.1; 424/531; 435/2; 252/174.17

[56] References Cited

U.S. PATENT DOCUMENTS 4,761,401 8/1988 Couchman et al. ............ 536/4.1
5,106,967 4/1992 Mazur ............................ 536/4.1

OTHER PUBLICATIONS

H. P. Kleine et al., *Carbohydrate Research*, vol. 142 (1985), pp. 333–337.
H. P. Kleine et al., *Carbohydrate Research*, vol. 182 (1988), pp. 307–312.
J. Banoub et al., *Can. J. Chem.*, vol. 57 (1979), p. 2085.
Tschierske et al., Amphiphilic carbohydrate based mesogens incorporating structural features of calamitic liquid crystals 8(6): 885–888 (1990).
Dainippon Ink Chem KK (published 1992).
Dale et al., "B–glucosidase: Substrate, Solvent, and Viscosity Variation as Probes of the Rate Limiting Steps", Biochem. 25: 2522–2529 (1986).

Primary Examiner—Ronald W. Griffin
Attorney, Agent, or Firm—Felfe & Lynch

[57] ABSTRACT

Novel compounds having the general formula

S—Ar—X in which
S denotes a saccharide residue
Ar denotes an aryl residue and
X denotes a straight-chained or branched alkyl residue with 2 to 20 carbon atoms, provided that the aryl residue may not be a 4-ethylphenyl, 4-isopropylphenyl, 4-sec.-butyl or 4-dodecylphenyl residue if the saccharide is a galactopyranoside residue, are interesting surface-active agents and are particularly suitable in diagnostic tests in order to clear serum.

15 Claims, 1 Drawing Sheet

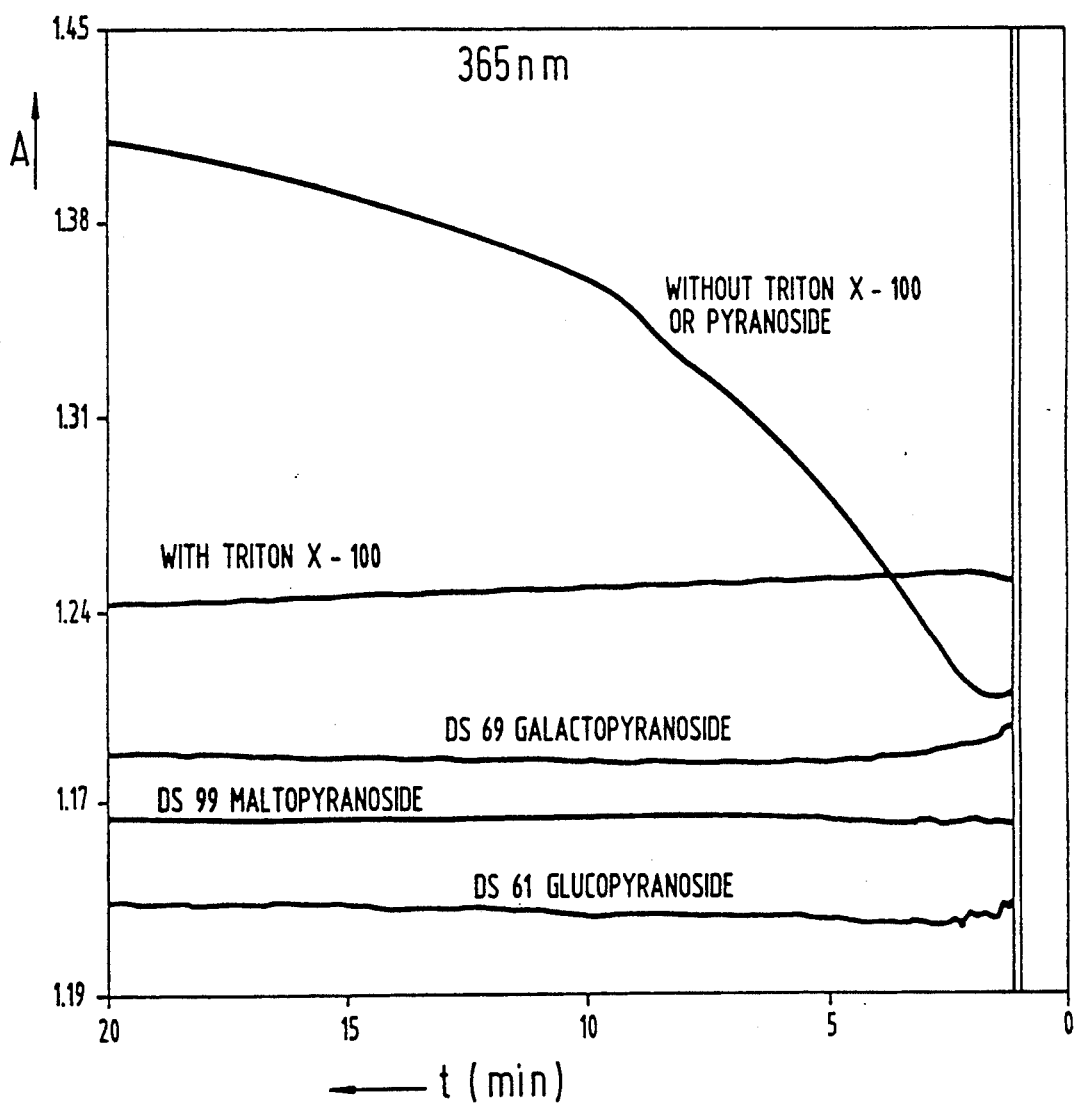

ALKYL-SUBSTITUTED ARYL-SACCHARIDES, SURFACE-ACTIVE AGENTS WHICH CONTAIN SUCH SACCHARIDES AND THEIR USE IN DIAGNOSTIC TESTS

The invention concerns new aryl-saccharides, surface-active agents which contain such saccharides as surfactants and their use in diagnostic tests.

The evaluation of diagnostic tests is often considerably interfered with by hydrophobic components which come into the test system via the body fluids to be analysed such as serum. The most frequent of such interferences are for example turbidities in the test system and non-specific interactions of hydrophobic components from the sample or the reagents with other components of the test. Thus attempts have already been made to avoid these interferences by using non-ionic surfactants of the alkyl ethoxylate and aryl ethoxylate type as auxiliary agents in diagnostic tests. Thus it is for example known from U.S. Pat. No. 4,275,151 that alkylphenoxypolyethoxyethanol with a polyoxyethylene chain of less than 20 oxyethylene units can be used as a surface-active substance in the determination of cholesterol esters which are present in blood serum bound to protein.

It is known from U.S. Pat. No. 4,810,630 that in enzyme-immunoassays which contain peroxidase conjugates a detergent can be added consisting of one or several polyoxyethylene ethers, and in particular Triton ® X-100, and thus improve the sensitivity of the test.

The surfactants which have been used up to now to eliminate the described interference in diagnostic test systems have, however, been solely technical products which are obtained by addition of ethylene oxide to the corresponding alcohols or phenols. However, this production process causes a large range of variation in the degree of ethoxylation and in the quality of the products. Moreover these substances contain different amounts of impurities depending on the lot such as peroxides, carbonyl compounds and heavy metal salts. All these impurities which are brought in by the surfactant can lead to undesired effects when using such test systems and thus to erroneous results.

Finally ethoxylated i-octylphenols are also regarded as being poorly biodegradable and can therefore not be disposed of in sewage plants. Thus for reasons of environmental protection they should be kept out of sewage.

Thus the object of the invention is to provide a non-ionic surfactant or a surface-active agent which eliminates or reduces interferences occurring in diagnostic tests caused by hydrophobic components and which does not have the aforementioned disadvantages.

Surprisingly it was found that this object can be achieved with a surface-active agent or a surfactant which contains aryl-substituted saccharides having the general formula (I)

$$S-Ar-X \qquad (I)$$

in which
S denotes a saccharide residue
Ar denotes an aryl residue and
X denotes a straight-chained or branched alkyl residue with 2 to 20 carbon atoms.

Such saccharides show a constant absorbance over a long time period in a test system to which lipids have been added.

The invention also concerns aryl-substituted saccharides having the general formula (I) provided that when the saccharide is a galctopyranoside residue, Ar—X may not, be 4-ethylphenyl, 4-isopropylphenyl, 4-sec.-butyl-phenyl or 4-dodecylphenyl.

Preferred saccharides are monosaccharides and oligosaccharides. Disaccharides and trisaccharides are in turn preferred oligosaccharides. Of the monosaccharides themselves, ethythrose, threose, arabinose, ribose, xylose, glucose, mannose, galactose and fructose are particularly preferred. Of the oligosaccharides, in particular of the disaccharides and trisaccharides, those are particularly preferred according to the present invention which contain units of these monosaccharides such as e.g. maltotriose. The saccharides contained in the compounds or agents according to the present invention are also understood to include corresponding derivatives such as glucuronic acid or sugar alcohols such as sorbitol and mannitol. The corresponding deoxy compounds such as deoxyribose, sorbose and rhamnose are also suitable as saccharide units in the compounds according to the present invention. Open as well as ring-shaped sugars such as furanoses and pyranoses are also suitable within the scope of the present invention.

Particularly preferred disaccharides are cane sugar, lactose, centibiose, melibiose, rutinose, sucrose, saccharose, maltose, cellobiose and trehalose. However, maltopyranoside, galactopyranoside and glucopyranoside are very especially preferred.

Among the aryl residues, phenyl residues and benzyl residues are particularly preferred. With respect to $C_2$-$C_{20}$ alkyl residues, $C_4$-$C_{18}$ residues are preferred, and $C_6$-$C_{12}$ alkyl residues are especially preferred. The alkyl residues can be branched or straight-chained and also have unsaturated bonds if desired. However, it is expedient that they are completely saturated. Nonyl and octyl and in particular iso-octyl residues are very especially preferred.

The aryl residues preferably carry the alkyl substituent in the para position on the sugar moiety. The aryl residue itself is linked to the sugar via all the suitable bonds.

However, preferred bonds are for practical purposes glycosidic $\alpha$-bonds and $\beta$-bonds.

The invention also concerns the use of the compounds and agents according to the present invention in diagnostic tests to reduce turbidity, in particular in lipaemic sera, and in order to keep such a turbidity constant at a low level.

The production of saccharides substituted with aryl residues is known to one skilled in the art and is preferably carried out according to the process described by H. P. Kleine et al., in Carbohydrate Research 142 (1985), 333–337. According to this, the saccharides are firstly converted to corresponding per-O-acetylated compounds by sodium acetate and acetic anhydride as described by C. S. Hudson and J. M. Johnson, J. Am. Chem. Soc. 37 (1915), 1270 and 1276. The acetates obtained in this way are converted into the corresponding bromide and reacted with the desired aryl compound in a phase transfer catalyzed reaction.

A further process with which the substances according to the present invention can be obtained is described by Kleine et al. in Carbohydrate Research 182 (1988), 307–312. A further process for the production of the substances according to the present invention is described by J. Banoub and D. R. Bundle in Can. J. Chem. 57, 2085 (1979). According to this, the completely acetylated sugar compounds are converted in methylene chloride at low temperatures directly into the desired product with the corresponding alkyl-substituted aryl compound under catalysis by a Lewis acid ($SnCl_4$).

The invention is elucidated further by the following examples.

EXAMPLE 1

Iso-octylphenyl-glucopyranoside is produced according to the process described by H. P. Kleine in Carbohydrate Research 142 (1985), 333-337.

For this 10 g 2,3,4,6-tetra-O-acetyl-α-D-glucopyranosyl-bromide is dissolved in 100 ml chloroform while stirring vigorously. The solution is heated under reflux and then a solution of 9.9 g iso-octylphenol, 5.53 g benzyltriethylammonium bromide in 35 ml 1.25 mol/l NaOH solution is added. After 3 hours the preparation is allowed to cool and 100 ml water is added. The organic phase is removed, shaken twice with 1.25 mol/l NaOH, dried and subsequently the solvent is evaporated off. A yellow oil is obtained.

The cleavage of the acetyl protective groups is carried out by dissolving and stirring the oil in a mixture of methanol, triethylamine and water in a ratio of 2:1:1. The solvent is distilled off and the product is purified by column chromatography. Iso-octylphenyl-glucopyranoside is obtained in a yield of 40%.

Iso-octylphenyl-galactopyranoside and iso-octylphenyl-maltopyranoside (as well as the corresponding 4-nonylphenyl-substituted analogues) are produced in an analogous manner.

EXAMPLE 2

The following reagent solutions were prepared: 1.530 g Tris, 800 mg sodium cholate and 1.50 g magnesium sulphate were dissolved in water and adjusted with (+)tartaric acid to pH 7.15 and made up to 200 ml with redistilled water. In addition 1 ml Intralipid ® (obtainable from the Pfrimmer Company, Erlangen) (20% fat emulsion for intravenous infusion) was dissolved in 27.57 ml redistilled water. A 0.7% lipid solution was obtained in this way.

For the detergent solutions 0.03 g Triton ®-X100, 0.03 g of the maltopyranoside obtained in example 1, galactopyranoside and glucopyranoside were added to 25 ml of the above reagent solution in each case.

In order to investigate the clearing of the lipid solution caused by the surfactants, 2.5 ml reagent/detergent solution and 0.05 ml lipid solution were pipetted into a cuvette (light path 1 cm) and measured in a photometer at a wavelength of 365 nm over time against 2.5 ml reagent/detergent solution with a 0.05 ml addition of redistilled water as a blank. The results are shown in FIG. 1.

This shows that when a surfactant or detergent is not added the absorbance increases continuously because of the increasing turbidity. Although the reference detergent Triton ®-X100 exhibits a constant clearing over time it is, however, at a substantially higher level of absorbance than with the readily biodegradable saccharides according to the present invention.

EXAMPLE 3

Clearing of lipaemic sera

The following reagent solution was prepared: 1.530 g Tris, 800 mg sodium cholate and 1.500 g magnesium sulphate were dissolved in water and adjusted with L(+)tartaric acid to pH 7.15 and made up to 200 ml with redistilled water. For the detergent solution, 0.03 g Triton ®-X100 or 0.03 g maltopyranoside were each added to 25 ml of the reagent solution.

The clearing effect of the surfactants was tested on human sera with different contents of triglycerides. The sera used contained ca. 200, 300, 500, 800, 1000 mg/dl triglycerides.

In order to investigate the clearing of the sera caused by the surfactants, 2.5 ml reagent/detergent solution and 0.05 ml serum were pipetted into a cuvette (light path 1 cm) and measured over time in a photometer. The results (optical density in mA at 365 nm) are shown in Table 1.

TABLE 1

| Reagents | A (4 min) (mA) | A (10 min) (mA) | A (20 min) (mA) |
|---|---|---|---|
| Serum 200 mg/dl | | | |
| Triton X-100 | 167 | 166 | 165 |
| Maltopyranoside | 146 | 141 | 140 |
| reag. sol. without surfactant | 166 | 164 | 164 |
| Serum 300 mg/dl | | | |
| Triton X-100 | 288 | 286 | 285 |
| Maltopyranoside | 251 | 250 | 248 |
| reag. sol. without surfactant | 300 | 298 | 299 |
| Serum 500 mg/dl | | | |
| Triton X-100 | 195 | 192 | 191 |
| Maltopyranoside | 170 | 168 | 166 |
| reag. sol. without surfactant | 196 | 195 | 196 |
| Serum 800 mg/dl | | | |
| Triton X-100 | 593 | 588 | 584 |
| Maltopyranoside | 572 | 569 | 563 |
| reag. sol. without surfactant | 651 | 652 | 658 |
| Serum 1000 mg/dl | | | |
| Triton X-100 | 553 | 546 | 543 |
| Maltopyranoside | 532 | 528 | 522 |
| reag. sol. without surfactant | 606 | 613 | 618 |

We claim:

1. Composition useful in reducing turbidity in a sample, comprising a surface active agent and a compound having the formula:

S—Ar—X, wherein

S is a saccharide residue;

Ar—X is an aryl residue; and

X is a straight chained or branched alkyl residue with 2 to 20 carbon atoms, with the proviso that where S is a galactopyranoside residue, Ar—X is not a 4-ethylphenyl residue, a 4-isopropylphenyl residue; a 4 sec-butyl residue or a 4-dodecylphenyl residue.

2. The composition of claim 1 wherein the aryl residue is a benzyl or phenyl residue.

3. The composition of claim 1 wherein S and X are in the para position with respect to each other on the aryl residue.

4. The composition of claim 2 wherein S and X are in the para position with respect to each other on the benzyl residue.

5. The composition of claim 1 wherein S is a monosaccharide, disaccharide or a trisaccharide.

6. The composition of claim 1 wherein S is selected from the group consisting of glucose, mannose, galactose, fructose, erythose, threose, arabinose, ribose, and xylose.

7. The composition of claim 1 wherein the S is selected from the group consisting of can sugar, lactose, cellobiose, trehalose, maltose, centibiose, melibiose and rutinose.

8. The composition of claim 1 wherein X is a C4-C18 alkyl residue.

9. The composition of claim 8 wherein X is a C6-C12 alkyl residue.

10. The composition of claim 9 wherein X is an octyl or a nonyl residue.

11. The composition of claim 1 wherein the aryl residue is linked to the saccharide via a glycosidic alpha or beta bond.

12. The composition of claim 1, wherein said compound is selected from the group consisting of iso-octylphenyl glucopyranoside, iso-octylphenyl maltopyranoside, 4-nonylphenyl glucopyranoside, and 4-nonylphenyl maltopyranoside.

13. Compound selected from the group consisting of iso-octylphenyl glucopyranoside, iso-octylphenylmaltopyranoside, 4-nonylphenylglucopyranoside and 4-nonylphenylmaltopyranoside.

14. Method for clarifying a serum sample comprising adding an amount of a composition useful in reducing turbidity comprising a surface active agent and a compound having the formula:

S—Ar—X, wherein

S is a saccharide residue;

Ar—X is an aryl residue; and

X is a straight chained or branched alkyl residue with 2 to 20 carbon atoms, with the proviso that where S is a galactopyranoside residue, Ar—X is not a 4-ethylphenyl residue, a 4-isopropylphenyl residue; a 4 sec-butyl residue or a 4-dodecylphenyl residue to said serum sample in an amount sufficient to reduce turbidity.

15. Method of claim 14 wherein said compound is selected from the group consisting of iso-octylphenyl glucopyranoside, iso-octylphenyl maltopyranoside, 4-nonylphenyl glucopyranoside, and 4-nonylphenyl maltopyranoside.

* * * * *